United States Patent [19]
Rochester

[11] Patent Number: 5,636,627
[45] Date of Patent: Jun. 10, 1997

[54] EQUIPMENT AND METHOD FOR GAS EXTRACTION IN GENERAL ANAESTHESIA

[75] Inventor: Noel J. Rochester, Gerrards Cross, England

[73] Assignee: N.J. Rochester Limited, Beaconsfield, England

[21] Appl. No.: 440,110

[22] Filed: May 12, 1995

Related U.S. Application Data

[63] Continuation-in-part of Ser. No. 133,116, Oct. 8, 1993, abandoned.

[30] Foreign Application Priority Data

Apr. 12, 1991 [GB] United Kingdom .................. 9107806

[51] Int. Cl.$^6$ ......................................... A62B 7/00
[52] U.S. Cl. ...................... 128/205.27; 128/910; 433/25; 454/63
[58] Field of Search .................. 128/203.12, 204.18, 128/205.27, 847, 849, 910, 863; 454/63, 65, 67, 189; 433/25

[56] References Cited

U.S. PATENT DOCUMENTS

| | | | |
|---|---|---|---|
| 2,418,473 | 4/1947 | Lambertsen | 128/205.26 |
| 3,537,447 | 11/1970 | Gauthier | 128/910 X |
| 3,813,092 | 5/1974 | Foster | 5/600 |
| 3,877,435 | 4/1975 | Bucalo | 128/843 |
| 3,877,691 | 4/1975 | Foster | 5/600 |
| 4,015,598 | 4/1977 | Brown | 128/205.25 |
| 4,038,913 | 8/1977 | Earley . | |
| 4,082,092 | 4/1978 | Foster | 128/847 |
| 4,276,819 | 7/1981 | Goldman | 454/56 |
| 4,446,861 | 5/1984 | Tada | 128/910 X |
| 4,780,927 | 11/1988 | Clayton | 15/345 |
| 4,840,169 | 6/1989 | Folsom | 128/863 |
| 4,852,468 | 8/1989 | Harris | 454/56 |
| 4,860,644 | 8/1989 | Kohl et al. | 454/65 |
| 4,865,049 | 9/1989 | Gatti | 128/849 |
| 4,936,318 | 6/1990 | Schoolman | 128/847 |
| 4,949,714 | 8/1990 | Orr | 128/200.24 |
| 5,074,284 | 12/1991 | Lelong | 126/519 |
| 5,125,939 | 6/1992 | Karlsson | 55/316 |
| 5,263,897 | 11/1993 | Kondo et al. | 454/189 |

FOREIGN PATENT DOCUMENTS

| | | | |
|---|---|---|---|
| 53506/90 | 10/1990 | Australia . | |
| 185230 | 6/1986 | European Pat. Off. | 433/25 |
| 2629689 | 1/1977 | Germany | 454/65 |
| 3004392 | 8/1981 | Germany | 454/65 |
| 227196 | 8/1943 | Switzerland | 454/65 |
| 329350 | 2/1972 | U.S.S.R. | 454/65 |
| 879179 | 11/1981 | U.S.S.R. | 454/65 |
| 2205501 | 12/1988 | United Kingdom . | |
| 2219203 | 12/1989 | United Kingdom . | |
| WO90/10486 | 9/1990 | WIPO . | |

*Primary Examiner*—Vincent Millin
*Assistant Examiner*—William J. Deane, Jr.
*Attorney, Agent, or Firm*—Davis and Bujold

[57] ABSTRACT

Contaminated air in general anaesthesia is extracted via a hemispherical hood 1 located closely over the patient. The hood 1, which is of a thin-wall transparent-shell form, is mounted for hand-touch variation of its orientation on an arm 2 which is carried by a telescopic column 3 that allows for height adjustment. The arm 2 extends from a unit 18 that allows the hood 1 to be swung horizontally about the column 3, and gas is drawn from the hood 1 near its open mouth 6 via a low-down port 7 (FIGS. 3 to 5) that is coupled through the arm 2 and column 3 to a fan unit 4. Relief 23 of the bottom margin of the hood 1 may be used to enhance access to the patient, and for maneuverability the column 3 is trolley-mounted or adjustable laterally on a fixed track 35 (FIGS. 9 and 10).

12 Claims, 5 Drawing Sheets

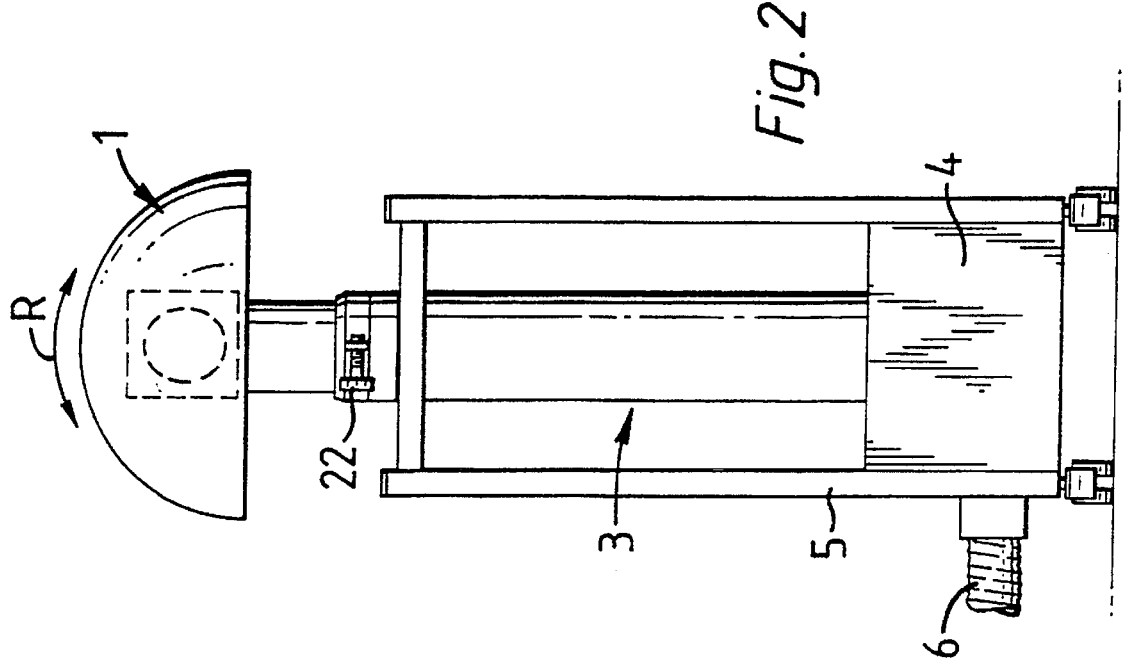
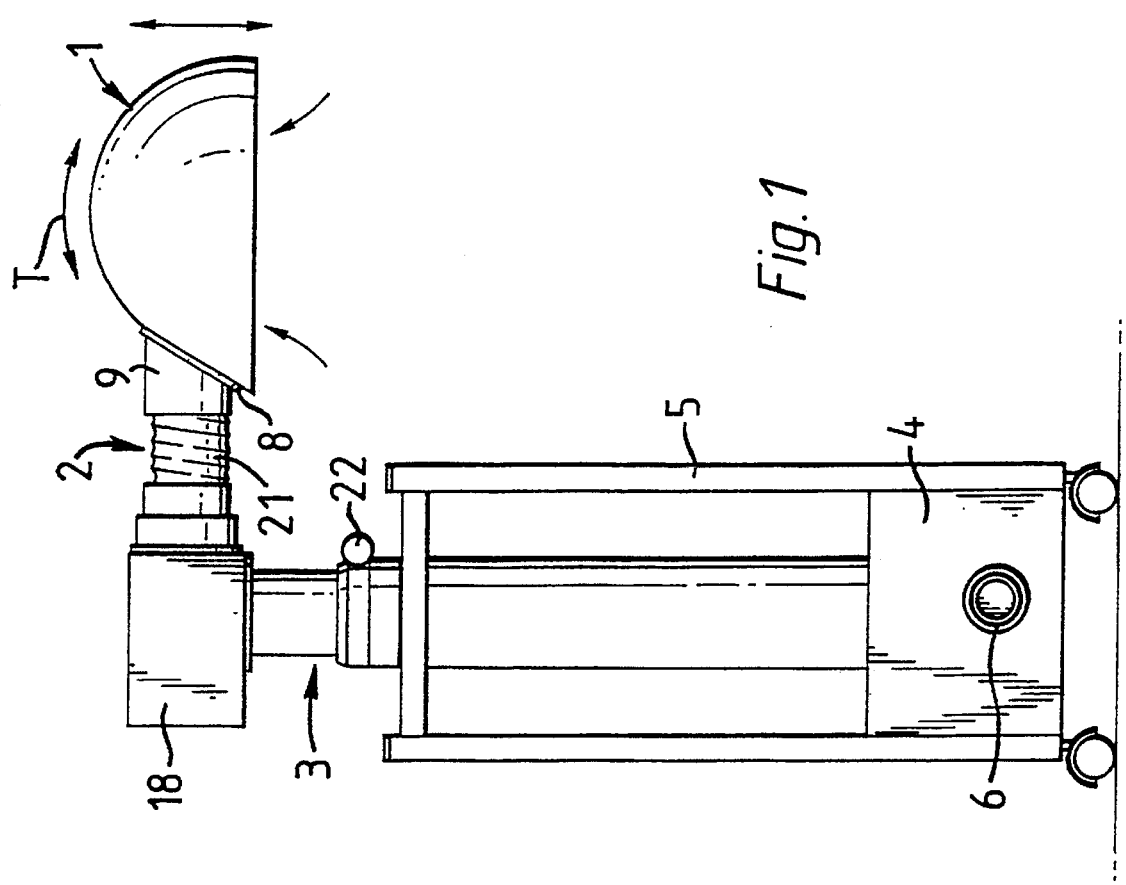

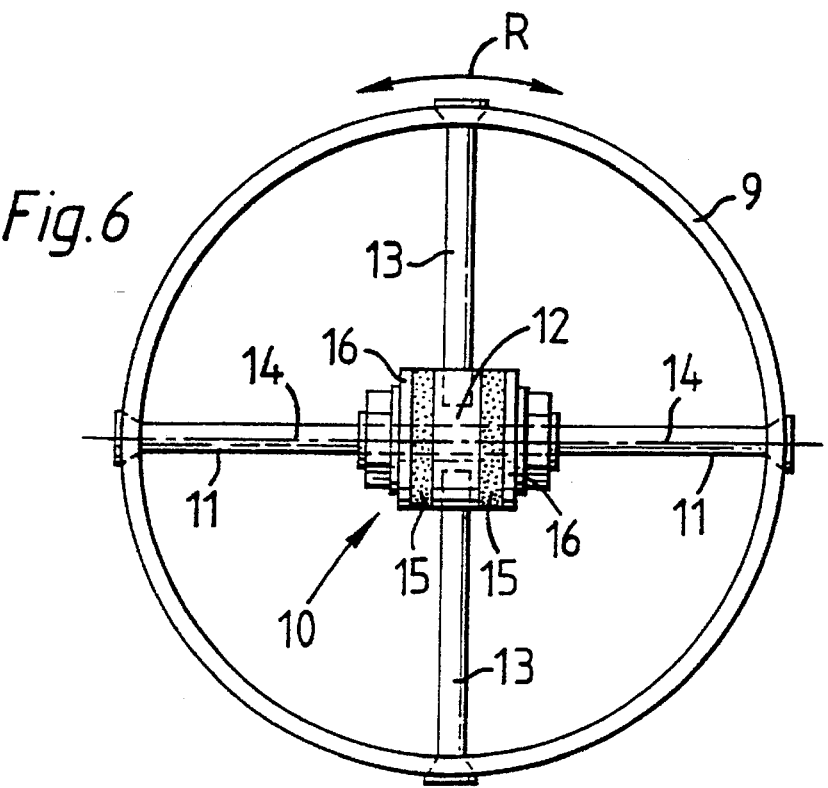
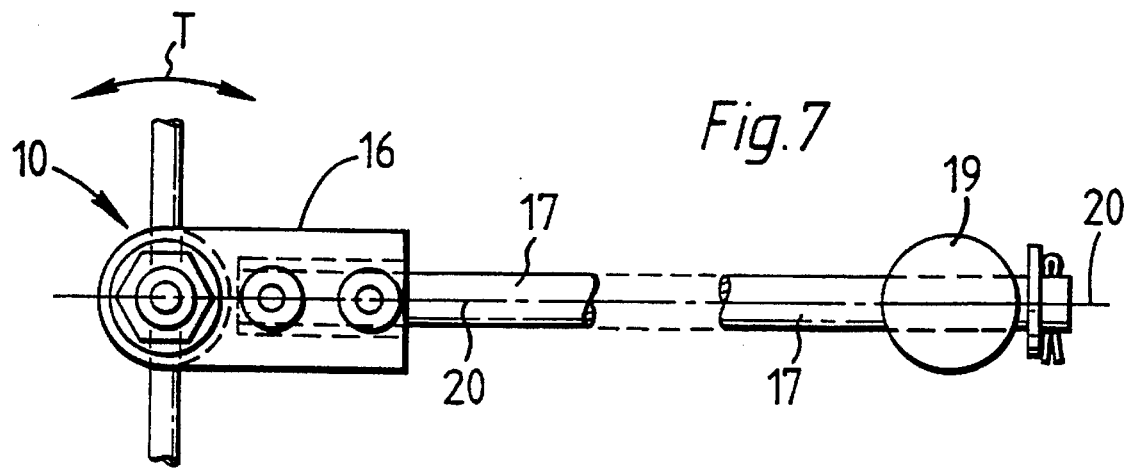

EQUIPMENT AND METHOD FOR GAS EXTRACTION IN GENERAL ANAESTHESIA

This is a continuation-in-part of application Ser. No. 08/133,116 filed on Oct. 8, 1993 now abandoned.

BACKGROUND OF THE INVENTION

This invention relates to gas extraction.

The invention is concerned especially with extraction of waste gas in the context of general anaesthesia. In general anaesthesia there is danger of the anaesthetist and others attending on the human or animal patient, being themselves affected by the gas administered. This danger can arise from leakage occurring from the mask or other means used to administer the gas, and also from residual gas expired by the patient.

The adverse effects on the health and performance of anaesthetists and others exposed in their work to anaesthetic gases has been recognised for many years, and proposals involving shields have been made for reducing these effects. In particular, proposals have been made for extracting gas from around the patient's mouth and nose, and for shielding the one or more attendants located nearby, using a generally-flat transparent screen between them and the patient. Such proposals, however, have been found generally unsatisfactory owing to the obstructive nature and general inefficiency of the extraction equipment and shielding.

It is one of the objects of the present invention to provide gas-extraction equipment and methods that may be used with advantage over known gas-extraction equipment and methods, in the context of general anaesthesia.

SUMMARY OF THE INVENTION

According to the present invention there is provided gas-extraction equipment and a method of gas-extraction wherein the collection of gas for extraction is via the open mouth of a transparent hood, and the hood is of a generally-domed form.

The use of a transparent hood of generally-domed form for gas collection, has been found to be of especial advantage in the context of surgery and other procedures where anaesthetic gas is involved; it may in this regard find application generally in dental surgeries, in anaesthetic administration and operating rooms, and in post-surgery recovery areas. More particularly, view of the patient through the hood can be uninterrupted over a wide field, whilst enabling efficient collection of gas and contaminated air from around the patient's mouth and nose. The domed form of the hood provides a substantial reservoir-volume over the patient into which such gas and air may accumulate during the drawing-off process, so as to reduce the likelihood of spillage outwardly from the hood.

The dome-form of the hood may be generally spheroidal, however other dome-forms, for example based on conical or part-conical shapes, may be used. In essence, the choice of form is related to providing a significant enclosed volume within the hood above the open mouth, together with good undistorted and uninterrupted visibility through it. It has been found that these requirements can be readily satisfied using a generally-hemispherical shell for the hood. Withdrawal of gas from the hood may with advantage be via a port located low down in the hood adjacent the open mouth.

The hood may be mounted to extend from an arm and to be selectively adjustable in orientation with respect to the arm. The arm may be carried by a telescopic column for height adjustment of the hood, and in this case the path for the extracted gas may extend from the hood internally of the arm and column. For manoeuvrability, the arm and column may be trolley-mounted, or may be mounted on a track that enables movement laterally of the column.

BRIEF DESCRIPTION OF THE DRAWINGS

Examples of gas-extraction equipment and methods, in accordance with the present invention, will now be described with reference to the accompanying drawings, in which:

FIGS. 1 and 2 are side and front elevations respectively, of portable gas-extraction equipment according to the invention;

FIGS. 6 and 7 are front and side views, respectively of a swivel-joint mounting used for the transparent domed-hood in the gas-extraction equipment of FIGS. 1 and 2;

DESCRIPTION OF THE PREFERRED EMBODIMENTS

Figure 3:
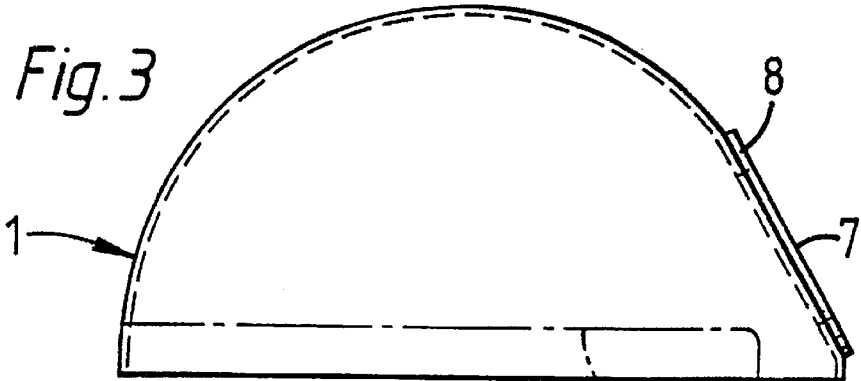
FIGS. 3 to 5 are respectively a side elevation, a rear elevation and a plan of the transparent domed-hood used in the gas-extraction equipment of FIGS. 1 and 2.

The gas-extraction equipment to be described with reference to FIGS. 1 and 2 may find application in dental surgery, and will be described in this context. However, the invention is not in general limited to this, and indeed the equipment to be described may be used in other contexts whether surgery is to the head or other parts of the body of a human or animal patient. The likelihood of those attending the patient being affected by the anaesthetic gas is intensified where dental surgery or other surgery to the head is being carried out, by virtue of the essential proximity of the surgeon as well as the anaesthetist, to the region of administration of the gas and exhalation by the patient.

The gas-extraction equipment to be described is adapted to reduce that likelihood without obstructing view of the site of surgery or unduly limiting access to it.

Referring to FIGS. 1 and 2, the gas-extraction equipment involves a gas-collection hood 1 that extends from a generally-horizontal tubular arm 2. The arm 2 projects from a tubular column 3 which is mounted to extend vertically upwards from an electrically-driven pump or fan unit 4 carried by a trolley 5. The fan unit 4 draws air from the collection hood 1 along the arm 2 and down the column 3 to exhaust it remotely through outlet ducting 6.

Figure 4:
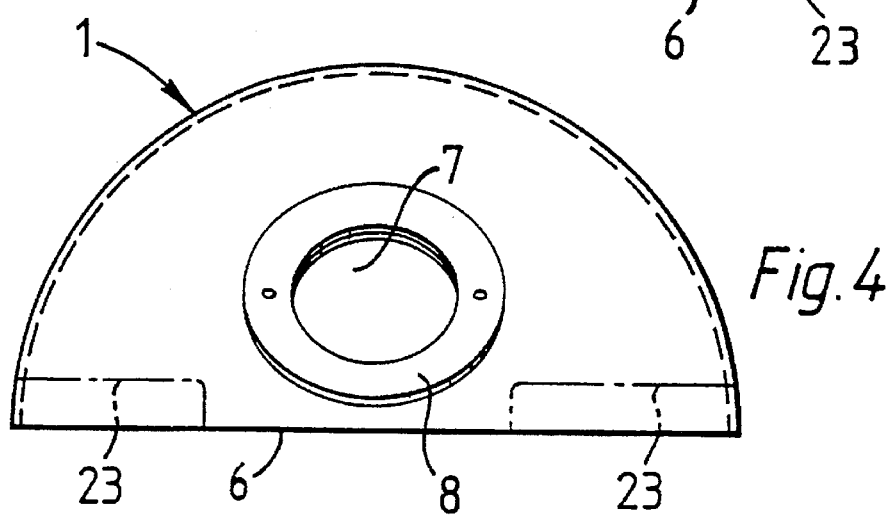
Figure 5:
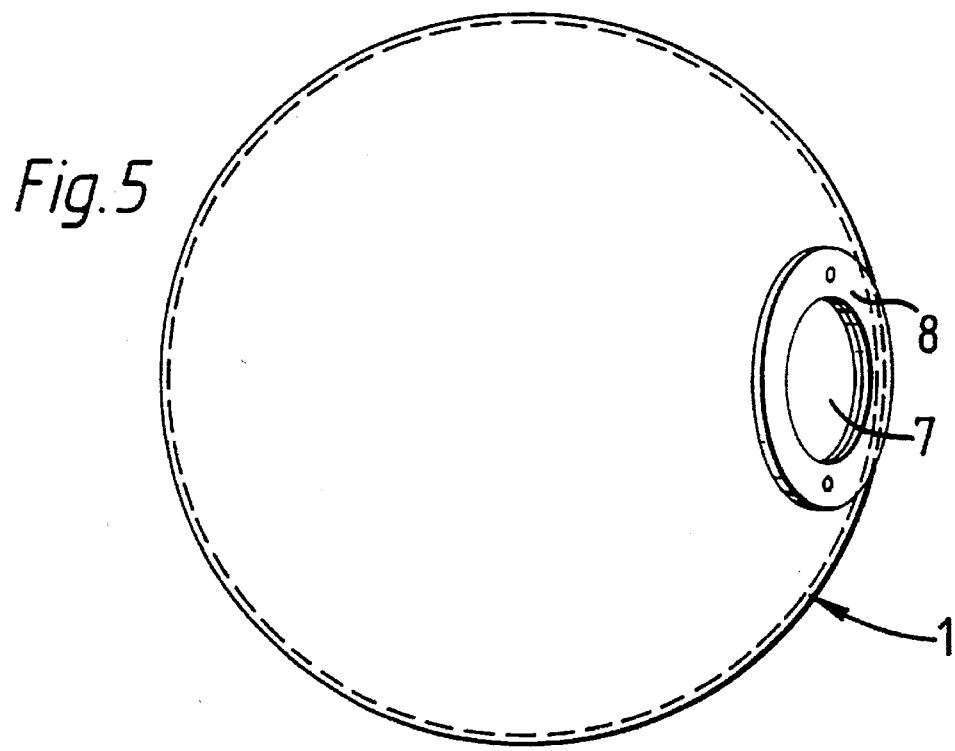

The hood 1, as shown in FIGS. 3 to 5, is of a clear acrylic resin having a thin-wall, but substantially rigid, shell construction with a circular, open mouth 6'. The shell, which may, for example, be of polymethyl methacrylate and have a wall-thickness of 4 mm (0.16 inches) and a diameter within the range 300–380 mm (11.81–14.96 inches), is of a domed form that is generally hemispherical except rearwardly where it is flattened and has a circular outlet opening or port 7. The port 7 is located low in the hood 1 close to the open mouth 6', and has an encircling annular flange 8 by which the hood 1 is releasably coupled to the arm 2. The bottom of the port 7 is as low as practical, for example within about 20 mm (0.79 inches) of the bottom edge defining the open mouth 6' of the hood 1, and its diameter is about 95–100 mm (3.74–3.94 inches).

The coupling between the hood 1 and the arm 2 is made via a short length of substantially-rigid tubing 9 that is clamped to the flange 8 and houses a swivel joint 10 close to the hood 1. The joint 10, which is illustrated only in FIGS. 6 and 7, allows the orientation of the tubing 9 and its attached hood 1, to be adjusted angularly in tilt (indicated by arrows T in FIGS. 1 and 7), as well as in rotation (indicated by arrows R in FIGS. 2 and 6).

Referring to FIGS. 6 and 7, the swivel joint 10 is mounted centrally within the tubing 9 on a diametrically-extending shaft 11. A central bush 12 of the joint 10 is rotatable on the shaft 11 and is coupled to the tubing 9 at right angles to the shaft 11 by support arms 13 so as to enable the tubing 9 to tilt about the shaft-axis 14. Friction pads 15 are clamped to either side of the bush 12 by plates 16 that are carried by the shaft 11, so as to restrain the bush 12, and with it the tubing 9 and attached hood 1, from tilting (T) about the axis 14 except under hand pressure.

The plates 16 are secured to one end of a rod 17 that extends centrally the length of the arm 2. The rod 17 supports the assembly of the shaft 11, swivel joint 10, tubing 9 and attached hood 1, from within a unit 18 (FIG. 1) that tops the column 3. Within the unit 18, the rod 17 extends through a transversely-mounted arm 19 and is retained there with freedom to rotate about its own longitudinal axis 20. The freedom of the shaft 17 for rotation enables the assembly including the hood 1 to be rotated about the axis 20, so that the orientation of the hood 1 is adjustable in rotation (R) as well as in tilt (T). The balance of the assembly is such as to ensure that the hood 1 remains in the orientation to which it is adjusted by hand, and that only light hand pressure is required to be exerted on the hood 1 to change that orientation in tilt (T) and/or rotation (R).

The rod 17 is enclosed throughout the length of the arm 2 from the tubing 9 to the unit 18, by flexible tubing 21 so that gas drawn through the hood 1 is passed to the column 3 without obstruction, for any hood-orientation. The unit 18 houses a rotatable joint to allow the tubing 9 to rotate about the rod 17 when the orientation of the hood 1 is adjusted, as well as bearings to enable the arm 2 to be swung round to any convenient location about the vertical column 3. Frictional restraint keeps the arm 2 from moving too easily from wherever it is placed in this respect, yet allows for displacement by easy touch of the hand. (Instead of the unit 18 being rotatable relative to the column 3, the column 3 may itself be mounted for rotation about the vertical, so that adjustment of the angular position of the arm 2 in the horizontal is achieved by rotation of the unit 18 and column 3 together as one, relative to the trolley 5. Furthermore, instead of providing for the rod 17 to rotate for adjustment of the hood 1 in rotation (R), the swivel joint 10 may be replaced by a universal joint mounted on a fixed rod.)

The column 3 is telescopic, allowing for variation of its length using a clamp control 22 (or alternatively, an internal brake device). This enables the height of the arm 2 to be adjusted to whatever is most convenient for optimum location of the hood 1 during use.

Figure 8:
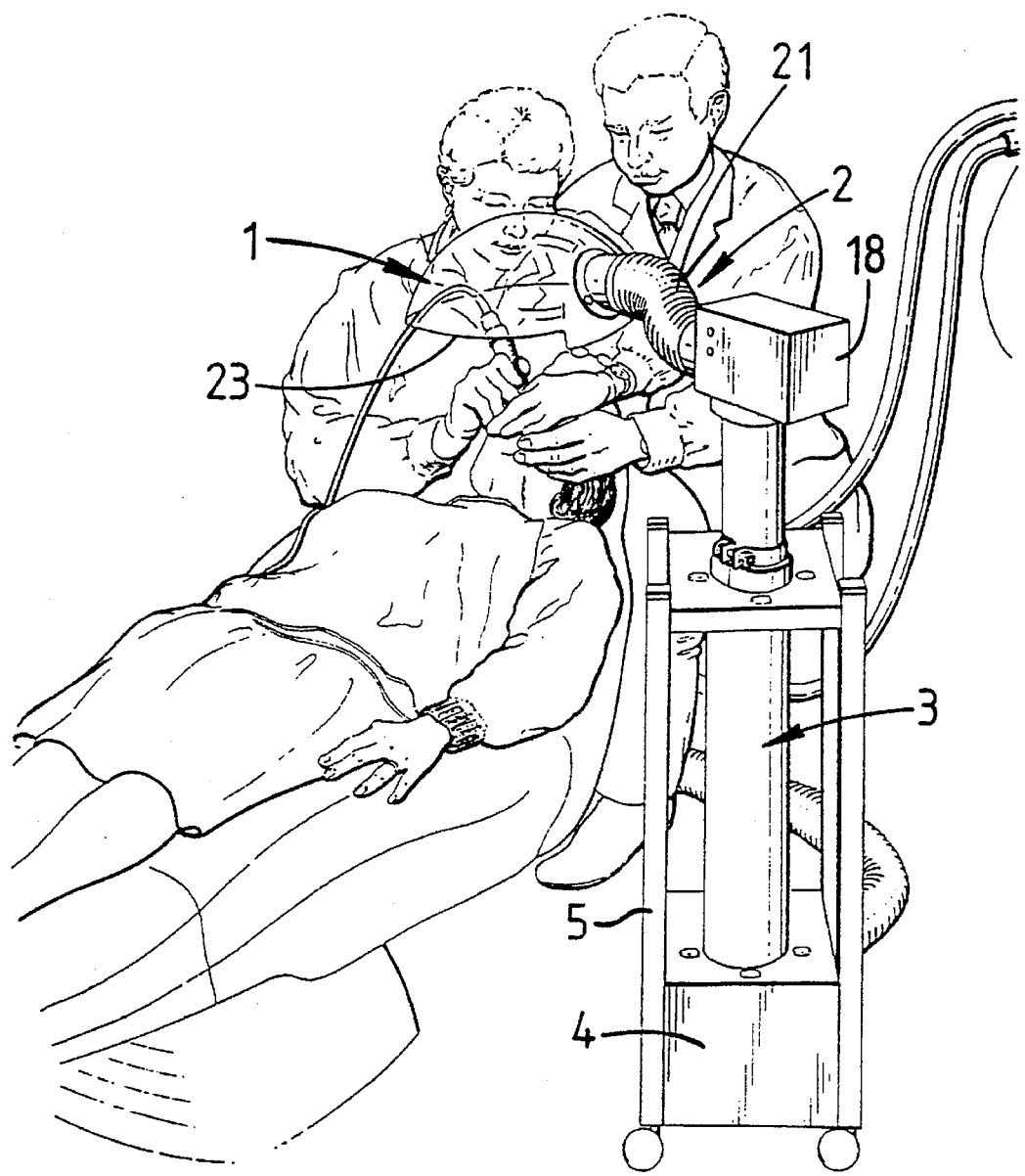
FIG. 8 illustrates use of the gas-extraction equipment in a surgical operation.

The manner in which the equipment may be used during the course of dental surgery is illustrated in FIG. 8, this showing the surgeon and anaesthetist located near the patient's head and shielded by the hood 1. Gas leaking from the mask used to administer the anaesthetic and mixed with gas and carbon dioxide exhaled by the patient, is drawn up into the hood 1 by the pump or fan unit 4, to be carried away via the tubing 21 and column 3 and thence for safe disposal into the atmosphere via the ducting 6.

The hood 1 can be located close to the patient over the patient's nose-mouth region, and this enables high efficiency of gas extraction to be achieved without the necessity for high air-movement and the distracting noise this normally creates. Although most of the gas-contaminated air and carbon dioxide is drawn off directly through the large-bore port 7, the domed configuration of the hood 1 provides a substantial reservoir-volume over the patient's head into which such gases can accumulate temporarily during the drawing-off process. This enables the equipment to keep undesired spillage of gasses outwardly from beneath the hood 1 to a minimum, notwithstanding the normal pulsating breathing pattern of the patient.

The surgeon and the anaesthetist both have an unobstructed view of the patient from virtually all angles, through the transparent hood 1; the spherical dome surface and the low location of the port 7 in the hood 1, ensure that distraction (in spite of any reflection in the hood-surface) and interruption of view are kept to a minimum. They also have ready access under the hood 1 for carrying out the necessary surgical and other procedures. In the latter respect, access under the hood 1 can be increased where desired by a modification shown adopted in FIG. 8 and involving relief 23 of the bottom margin of the hood 1 forwardly from its coupling to the arm 2. This modification of the hood 1 is also illustrated in FIGS. 3 and 4 where the portion cut away for the relief 23 is delineated in broken line.

Once the trolley 5 has been stationed, slight pressure by hand on the hood 1 is all that is necessary to adjust the location and orientation of the hood 1 to the best advantage to shield those in attendance whilst allowing them clear access to the patient. The hood 1 can be rapidly swung out of the way simply by pushing it away by hand in the event of emergency or other circumstances calling for its removal. Where appropriate, the equipment rather than being trolley-mounted, may be provided as a fixture, for example mounted on an adjustable spring-balanced arm or on a track. Equipment installed in this latter way, for example, in a dental surgery, is shown in FIGS. 9 and 10.

Figure 9:
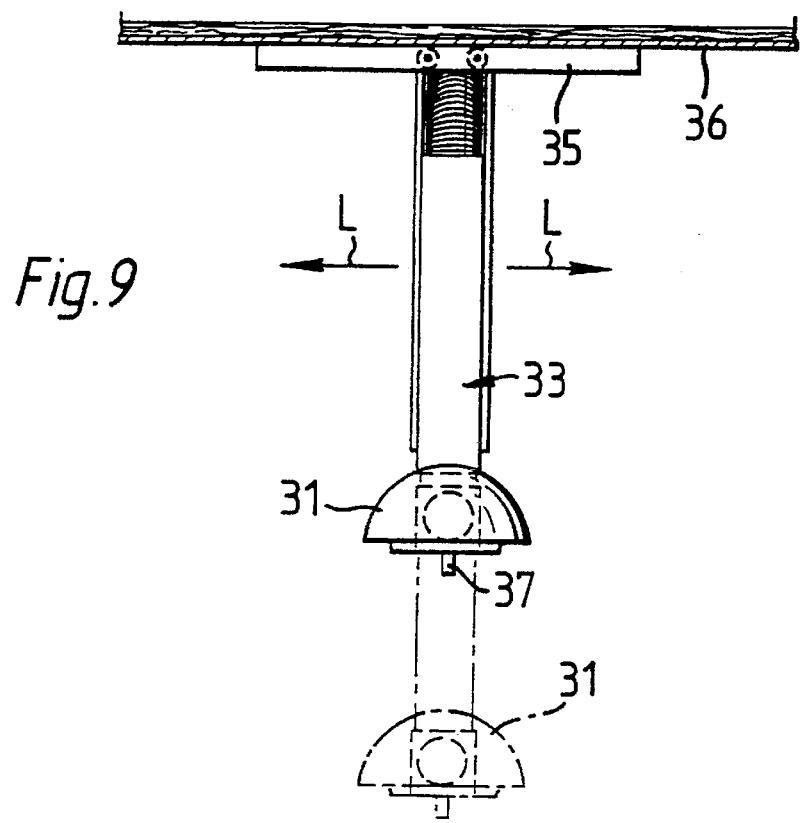
FIGS. 9 and 10 illustrate an alternative, ceiling-mounted form of gas-extraction equipment according to the invention.
Figure 10:
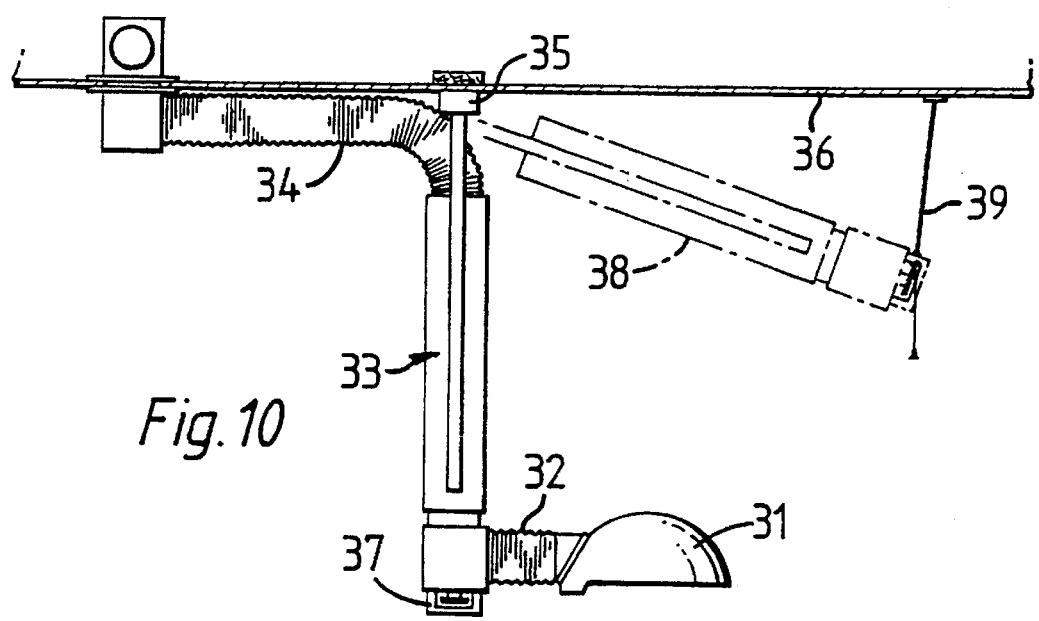

Referring to FIGS. 9 and 10, the hood 31 in this case is carried by an arm 32 that is coupled via a ceiling-mounted telescopic column 33 to exhaust ducting 34. The hood 31 is adjustable in both rotation and tilt with respect to the arm 32, and the column 33 is mounted for movement along a track 35 that is secured to the surgery ceiling 36. The track-mounting of the column 33 allows its position and that of the hood 31 to be adjusted laterally (as indicated by the arrows L in FIG. 9). The length of the column 33 is adjustable (indicated in broken line in FIG. 9) to allow for variation in height of the hood 31.

The column 33 contains a brake mechanism (not shown) which is normally engaged to restrain change of column-length. A release-control 37 of the brake mechanism is located at the bottom of the column 33, and is operative when gripped by hand to allow the column 33 to be extended or contracted in length simply by pulling it down or pushing it up. The telescopic movement of the column 33 is balanced using a constant tension spring (not shown) so that adjustment of column-length requires only a light pressure up or down on the gripped control 37. Once the length of the column 33 has been adjusted as desired, release of grip on the control 37 re-engages the brake mechanism to hold the column 33 at that length.

As indicated generally by broken line 38 in FIG. 10, the column 33 and arm 32 (with the hood 31 removed when not in use) may be stowed out of the way simply by swinging them upwardly for attachment to a ceiling-fitting 39.

A substantial part of the plant used and costs incurred for air-conditioning and ventilating surgical-operating rooms, conventionally relate to the removal of waste anaesthetic gas, required to maintain a safe atmosphere within those rooms. It has been found that savings in plant and costs can be made when equipment of the present invention is utilised, and that safety can be greatly improved. More especially, measurements taken when using equipment constructed as shown in the drawings in normal operation procedures involving nitrous oxide, have shown time-weighted average values for the nitrous oxide in the ambient atmosphere at the attendants' breathing level, of less than 50 parts per million; without the benefit of the gas-extraction equipment the corresponding values are of the order of 2,000 parts per million.

Although the invention has been described above primarily in the context of anaesthesia, it may be applied more generally. In particular, it may find application, for example, in pathology to shield the pathologist not only from gases and vapours hazardous to health but also from unpleasant odours; it may be applied in the latter respect also, in a veterinary context.

I claim:

1. Gas-extraction equipment for extracting gas from a region of air-contamination, said equipment comprising:

(a) a hood for collecting the gas for extraction from said region, said hood including a transparent shell that has an open mouth for location over said region to admit the gas into the hood from said region, said shell comprising a domed wall that is of substantially hemispherical configuration and has a port therethrough, said port being located closely adjacent the mouth to facilitate maximum visibility through the hood during use of said equipment;

(b) an arm for supporting the hood;

(c) means mounting the shell on the arm with the shell projecting from the arm, the mounting means including a selectively-adjustable coupling to interconnect the arm with the domed wall at said port, said coupling being selectively adjustable for varying the orientation of the shell with respect to the arm in locating the open mouth of the domed shell over said region; and (d) means coupled to the hood at the port for withdrawing gas collected within the shell, through said port.

2. The gas-extraction equipment according to claim 1 wherein the domed wall has a flattened portion bounding said port, and the mounting means includes a flange encircling the port within said flattened portion for connecting said coupling to the arm.

3. The gas-extraction equipment according to claim 1 wherein said coupling includes means defining first and second axes extending transversely and longitudinally, respectively, of the arm, and a swivel joint for selective adjustment of the domed shell in tilt about the first axis and in rotation about the second axis.

4. The gas-extraction equipment according to claim 1 wherein the means for withdrawing gas collected within the shell includes means defining a flow path for the gas extending internally of the arm from the shell.

5. The gas-extraction equipment according to claim 1 further including a telescopic column for carrying the arm, and wherein the arm is carried by the column with the arm projecting substantially transversely of the column.

6. Gas-extraction equipment for the extraction of gas from an area of manipulative procedure, said gas-extraction equipment comprising:

(a) a hood for collecting gas from said area, the hood comprising a transparent shell of a domed configuration to define a gas-collection chamber of the hood, said domed shell having an open mouth for admitting gas to said chamber and a port for venting gas from the chamber;

(b) mounting means coupled to the shell at said port, said mounting means including means for supporting the shell to shield said area with the open mouth over said area; and (c) suction means vented through the shell at said port for drawing off from the hood gas collected in said chamber; the domed configuration of the transparent shell being substantially hemispherical in shape for integrity of vision of said area through the shell throughout a wide angular range, said port being located in said domed shell closely adjacent to said open mouth for minimum obstruction to a user viewing said area through the shell during use of said gas-extraction equipment, and said mounting means including means for selective adjustment of the orientation of the shell relative to said area.

7. The gas-extraction equipment according to claim 6 wherein said mounting means includes an arm for supporting the shell, and a swivel joint for mounting the shell to project from the arm with a selectively adjustable orientation with respect to the arm.

8. The gas-extraction equipment according to claim 7 including a column of selectively adjustable length, means mounting the arm on the column to extend laterally of the column, and means defining a path for extracted gas, said path extending from the hood internally of the arm and column.

9. The gas-extraction equipment according to claim 8 including a trolley and means mounting the column on the trolley.

10. The gas-extraction equipment according to claim 8 including an elongate track and means mounting the column on the track for movement of the column laterally of the column.

11. A method of shielding surgical staff from a waste gas during administration of anaesthetic gas to a patient, said method comprising the steps of:

(a) providing a gas-collection hood that comprises a transparent shell having a substantially hemispherically-domed configuration to define a gas-collection chamber of the hood, said shell having an open mouth for admitting gas to said chamber;

(b) positioning the hood with the open mouth over the face of the patient to admit gas exhaled by the patient to said chamber, said positioning including locating the domed shell intermediate the surgical staff and the patient's face to the extent that the surgical staff view the patient's face via the transparent hemispherically-domed shell and providing access under the hood for hand contact with the patient's face; and (c) at least during administration of anaesthetic gas to the patient, drawing off from the hood gas collected in said chamber.

12. A method of gas-extraction from a region of air-contamination, wherein the collection of gas for extraction is via the open mouth of a transparent hood, the hood comprising a transparent shell that is mounted to extend from an arm with a selectively-adjustable orientation with respect thereto, the method of gas-extraction comprising the steps of:

(a) locating the hood over said region with said mouth open over said region to collect the gas within the shell; and (b) drawing off the collected gas from within the shell via a venting port through the shell;

and wherein the transparent shell is of a hemispherically-domed configuration, said venting port is located low down on the shell adjacent said open mouth, and the aforesaid mounting of the hood to the arm is effected adjacent the open mouth low down on the domed shell at the location of the venting port in the shell such that view through the hood into the region encompassed by the open mouth is substantially unobstructed and undistorted from substantially all angles over and around the domed shell away from the port.

* * * * *